United States Patent [19]

Green et al.

[11] 4,325,940

[45] Apr. 20, 1982

[54] ANTI-MICROBIAL, COSMETIC AND WATER-TREATING IONENE POLYMERIC COMPOUNDS

[75] Inventors: Harold A. Green, Havertown, Pa.; John J. Merianos, Middletown; Alfonso N. Petrocci, Glen Rock, both of N.J.

[73] Assignee: Kewanee Industries, Inc., New York, N.Y.

[21] Appl. No.: 119,948

[22] Filed: Feb. 8, 1980

Related U.S. Application Data

[63] Continuation-in-part of Ser. No. 29,778, Apr. 13, 1979, which is a continuation-in-part of Ser. No. 902,894, May 4, 1978, Pat. No. 4,190,644, which is a continuation-in-part of Ser. No. 744,617, Nov. 24, 1976, Pat. No. 4,089,977.

[51] Int. Cl.$^3$ ............... C07D 413/14; C07D 413/06; C07D 401/06; C07D 401/14
[52] U.S. Cl. ................ 424/70; 260/239 B; 260/244.4; 260/243.3; 260/326.5 L; 424/248.56; 424/248.57; 424/267; 424/274; 424/329; 544/82; 544/86; 546/186; 546/187; 564/292; 210/735
[58] Field of Search ............... 544/87, 82, 86; 260/567.6 H, 567.6 P, 326.5 L, 239 B, 244.4, 243.3; 424/70, 329, 267, 274, 248.56; 210/54; 546/186, 187; 564/292

[56] References Cited

U.S. PATENT DOCUMENTS

| | | | |
|---|---|---|---|
| 3,725,312 | 4/1973 | Panzer et al. | 260/567.6 P |
| 3,738,945 | 6/1973 | Panzer et al. | 260/567.6 P |
| 3,931,319 | 1/1976 | Green et al. | 260/567.6 P |
| 3,943,255 | 3/1976 | Newkirk | 424/329 |
| 4,024,311 | 5/1977 | MacDonald | 260/567.6 P |
| 4,027,009 | 5/1977 | Grier et al. | 424/78 |
| 4,054,542 | 10/1977 | Buckman | 260/567.6 P |
| 4,089,977 | 5/1978 | Green et al. | 424/329 |
| 4,111,679 | 9/1978 | Shair | 424/329 |
| 4,185,087 | 1/1980 | Morlino | 424/70 |
| 4,190,644 | 2/1980 | Green et al. | 424/70 |
| 4,213,960 | 7/1980 | Grollier et al. | 424/70 |

*Primary Examiner*—Mark L. Berch
*Attorney, Agent, or Firm*—Arthur A. Jacobs

[57] ABSTRACT

The use for anti-microbial, cosmetic and water-treatment of compounds of formula:

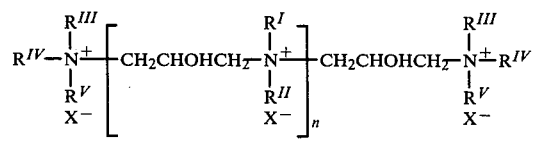

in which $R^I$ and $R^{II}$ and (I) the same or different monovalent, branched or unbranched, alkyl groups of from 1 to 18 carbon atoms, optionally substituted by from 1 to 2 hydroxyl groups; or (II) form a 5, 6 or 7 membered ring when taken together with N, or (III) form the N-morpholino group when taken together with N and an oxygen atom; wherein $R^{III}$, $R^{IV}$ and $R^V$ are (I) the same or different, branched or unbranched, alkyl groups of from 1 to 18 carbon atoms, optionally substituted by 1 or 2 hydroxyl groups, or (II) $R^{III}$ is a branched or unbranched alkyl group of from 1 to 18 carbon atoms optionally substituted by 1 or 2 hydroxyl groups and $R^{IV}$ and $R^V$ form a 5, 6 or 7 membered ring when taken together with N; or (III) $R^{III}$ is a branched or unbranched alkyl group of from 1 to 18 carbon atoms optionally substituted by 1 or 2 hydroxyl groups and $R^{IV}$ and $R^V$ form the N-morpholino group when taken together with N and an oxygen atom; wherein X is a halogen of atomic weight above 30; and wherein n is an integer of from 2 to 20.

56 Claims, No Drawings

ANTI-MICROBIAL, COSMETIC AND WATER-TREATING IONENE POLYMERIC COMPOUNDS

This application is a continuation-in-part of application Ser. No. 29,778, filed April 13, 1979, which is in turn, a continuation-in-part of application Ser. No. 902,894, and issued as U.S. Pat. No. 4,190,644, filed May 4, 1978, which is a continuation-in-part of application Ser. No. 744,617, filed Nov. 24, 1976 and issued as U.S. Pat. No. 4,089,977, dated May 16, 1978.

The disclosures of all of the above applications are incorporated by reference into this application.

The above-identified applications, as a whole, disclose the preparation of linear polymeric quaternary ammonium compounds of formula:

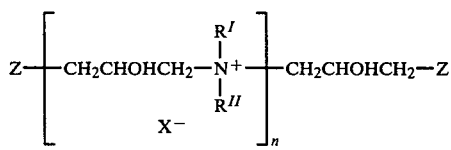

from approximately equimolar proportions of 1,3-dihalo-2-propanol of formula $X-CH_2CHOHCH_2-X$ and a 1,3-bis-tertiary amino-2-propanol of general formula:

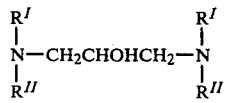

In the formula, $R^I$ and $R^{II}$ individually represent alkyl groups optionally substituted by one or two hydroxyl groups, and, when taken together, represent certain cyclic groups; X represents a halogen atom of atomic weight greater than 30; n is an integer from 2 to 20; and Z represents either X or $-N\ R^I R^{II}$.

An important feature of these polymers is that their termini must be either a halogen or a tertiary amino group. Each of these termini is reactive with one of the starting reactants in the polymerization reaction, whereby a terminal halogen may react with bis-tertiary amine to extend the chain by one unit and create a tertiary amine terminus, while a terminal tertiary amino group may react with the dihalo compound, thereby extending the chain by one unit and creating a halogen terminus.

The present invention relates to a new class of linear quaternary ammonium polymers in which both termini are quaternary ammonium groups. Since quaternary ammonium groups are incapable of undergoing chain propogation by reaction with either one of the starting monomers, the polymers are said to be "capped".

In one aspect of the invention, a 1,3-bis-tertiary amino-2-propanol of formula:

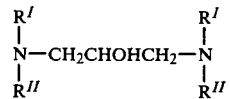

is permitted to react with a molar excess of a 1,3-dihalo-2-propanol of formula $X-CH_2CH_2OHCH_2-X$. The product of this reaction is

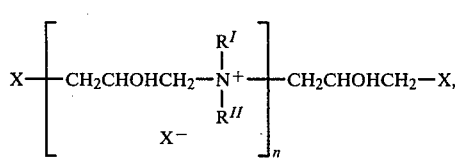

this product being a linear quaternary ammonium polymer in which both termini are halogen atoms.

In the formula shown above, $R^I$ and $R^{II}$ are (I) the same or different monovalent branched or unbranched alkyl groups of from 1 to 18 carbon atoms, optionally substituted by from 1 to 2 hydroxyl groups or (II) form a 5, 6 or 7 membered ring when taken together with N; or (III) form an N-morpholino group when taken together with N and an oxygen atom; X is a halogen of atomic weight above 30, and n is an integer of 2 to 20.

When the reaction has proceeded as far as it can go, the reaction mixture is separated from the excess dihalopropanol and the residual polymer is treated with a molar quantity of a mono-tertiary amine of formula $NR^{III}R^{IV}R^V$ equal to the number of equivalents of analytically determined organically bonded terminal halogen in the polymeric residue. The ensuing reaction between the polymer and the mono-tertiary amine acts to "cap" the polymer with two quaternary ammonium termini, as follows:

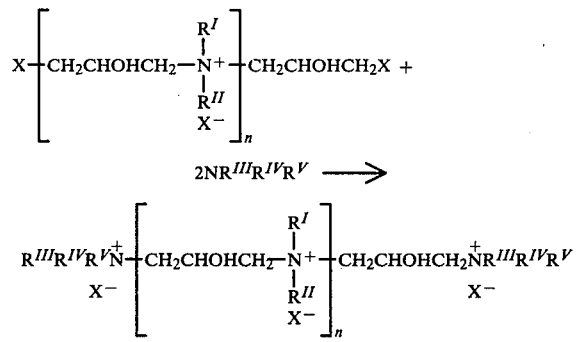

In the above equation $R^{III}$, $R^{IV}$ and $R^V$ are (I) the same or different branched or unbranched alkyl groups of from 1 to 18 carbon atoms optionally substituted by from 1 to 2 hydroxyl groups; or (II) $R^{III}$ is a branched or unbranched alkyl group of from 1 to 18 carbon atoms optionally substituted by from 1 to 2 hydroxyl groups, and $R^{IV}$ and $R^V$ form a 5, 6 or 7 membered ring when taken together with N; or (III) $R^{III}$ is a branched or unbranched alkyl group of from 1 to 18 carbon atoms optionally substituted by 1 to 2 hydroxyl groups, and $R^{IV}$ and $R^V$ form an N-morpholino group when taken together with N and an oxygen atom; X is a halogen of atomic weight above 30; and n is an integer of from 2 to 20.

Another aspect of the present invention lies in the provision of a single step method of preparing the polymeric products in which both termini are quaternary ammonium groups. In this method, the 1,3-dihalo-2-propanol is made to react with a mixture of a difunctional tertiary amine of the type $R^I R^{II} N-CH_2CHOHCH_2-NR^I R^{II}$ and a monofunctional tertiary amine, the molar ratio of the difunctional amine to the monofunctional amine being from about 2:1 to about 30:1, and their molar sum being approximately equal to the number of equivalents of reactive halogen. Both the mono-amine and the bis-amine are in the same reaction mixture. The product of this method is a linear quaternary ammonium polymer with quaternary ammonium termini having the same molecular representation as the product of the first process, but having a slightly different distribution of chain lengths, i.e. a slightly different distribution for the values of "n".

In both methods of preparation, chain propagation proceeds when a halogen terminus of the polymeric chain reacts with a tertiary amine terminus of the difunctional tertiary amine, thereby lengthening the chain by one unit, and creating a tertiary amine terminus. Further chain propagation is possible because the newly created tertiary amine terminus may react with a 1,3-dihalo-2-propanol molecule.

However, in the single step method, there is an alternative route. In the presence of a mono tertiary amine, the halogen terminus of the polymeric chain may react with the mono tertiary amine instead of the difunctional tertiary amine. This reaction produces a quaternary ammonium group which is incapable of further chain propagation with the dihalo reactant. The polymeric chain is thereby "capped".

In the above manner, any chain may become "capped" at either one terminus or at both termini, while other chains continue to lengthen.

Although the polymeric products by each of the two methods of preparation have the same molecular representation, it is possible that there may be a very slight difference between them, although this difference could not be detected when comparing the products for their anti-microbial, cosmetic, and water-treatment properties.

The source of differences in the products by the two methods of synthesis may arise from the fact that in one method the chains are apparently capped after having reached their maturity, whereas in the second method some chains may be capped very early in the presence of mono tertiary amine, whereas other chains are not capped until they have undergone a large number of propagation steps. Therefore, it might be expected that the value of "n" will have a slightly broader range in the one-step polymerization than in the two step polymerization, whereas the average molecular weight will be slightly greater in the product of the two-step reaction.

Methods of the above type for "capping" polymeric quaternary ammonium compounds are described in U.S. Pat. Nos. 3,931,319, 4,001,432; 4,012,446; 4,027,020; 4,036,959; 4,091,113; and 4,055,712.

All compounds were tested for anti-microbial activity by the method described in Example 4 of U.S. Pat. No. 4,089,977. They all had some anti-microbial activity, but the most potent anti-microbial was the compound in which $R^I$ equals $R^{II}$ equals $R^{III}$ equals $R^{IV}$ equals $R^V$ equals —$CH_3$.

All compounds were tested for hair-care properties by using deMeo hair tresses. The best hair-care products were those in which $R^I$ equals $R^{II}$ equals —$CH_3$ and $R^{III}$ equals $R^{IV}$ equals $R^V$ equals —$CH_3$ or —$CH_2CH_2OH$.

All compounds were tested as water-treatment materials by examining their flocculant properties using the method described in the aforementioned co-pending application Ser. No. 902,894. The best flocculants were the products in which
$R^I$ equals $R^{II}$ equals —$CH_3$, and $R^{III}$ equals $R^{IV}$ equals $R^V$ equals —$CH_3$ or —$CH_2CH_2OH$

EXAMPLE I

With constant stirring, 146 grams of bis-1,3-dimethylamino-2-propanol (1.0 mole), 160 grams of 1,3-dichloro-2-propanol (1.25 moles) and 300 grams of water were mixed. After the initial reaction subsided, the mixture was warmed slowly until it reached reflux temperature, where it was kept for 1½ hours. The mixture was then cooled, washed twice with cold methylene chloride, and the volatile material steam-distilled.

Analysis for non-ionic chlorine determined by subtracting analytically-determined ionic chloride from analytically-determined total chlorine, showed that the mixture contained about 0.24 mole of organically bound chlorine. It weighed about 600 grams and contained about 50% solids.

EXAMPLE II

The process described in Example I was repeated, except that 1 mole of 1,3-bis N-morpholino-2-propanol was used instead of 1,3-bis-dimethylamino-2-propanol. Also 1.25 moles of 1,3-dichloro-2-propanol and 390 grams of a 50—50 water-isopropanol mixture were used. The product contained about 0.20 mole of organically bound chlorine. It weighed about 775 grams, and contained about 50% solids.

EXAMPLE III

With constant stirring, about 60 grams of the product from Example I (a portion calculated to contain about 0.05 mole of organically bound chlorine) was mixed with about 40 grams of a 50—50 mixture of isopropanol and water containing about 6 grams (0.1 mole) of trimethylamine. The mixture was heated to the boiling point, and after 15 minutes it was kept at reflux for about one hour.

The product contained practically no organically bound chlorine. It weighed about 96 grams and contained about 30% solids.

It should be noted that about twice the theoretical quantity of trimethylamine was used because this tertiary amine is volatile under these conditions, and allowance was made for loss due to evaporation.

EXAMPLE IV

The procedure of Example III was repeated except that the product was steam-distilled to remove excess trimethylamine. Except for the fact that the product had only about 25% solids, no other difference was detected from the product of Example III with respect to anti-microbial, hair-care, and water treatment properties.

EXAMPLE V

The process described in Example III was repeated, except that the theoretical quantity of triethanolamine (7.6 grams, 0.05 mole) was substituted for trimethylamine.

EXAMPLE VI

The process described in Example III was repeated, except that the theoretical quantity of N-methylmorpholine (5 grams; 0.05 mole) was substituted for the trimethylamine.

EXAMPLE VII

The process described in Example III was repeated except that 0.05 mole of the product of Example II was used as the starting bis-amine, instead of the product from Example I.

EXAMPLE VIII

The process described in Example V was repeated, except that 0.05 mole of the product of Example II was used as the starting bis-amine instead of the product from Example I.

EXAMPLE IX 129 grams of 1,3-dichloro-2-propanol (1.0 mole) was added slowly to a mixture of 132 grams of 1,3-bis-dimethylamino-2-propanol (0.9 mole), 15.2 grams of triethanolamine (0.1 mole) and 276 grams of water. The mixture was heated slowly to boiling with constant stirring and kept at reflux temperature for about 2 hours. Analysis showed that the product contained practically no organically bound chlorine, and had about 50% solids.

EXAMPLE X

The process described in Example IX was repeated, except that 30.4 grams of triethanolamine (0.2 mole) and 260 grams of water were substituted for the original quantities.

The properties of the product appeared to be identical to the properties of the product of Example IX with respect to anti-microbial activity, hair-care, and water treatment.

EXAMPLE XI

The process described in Example IX was repeated except that 97 grams of 1,3-bis-dimethylamino-2-propanol (0.67 mole) and 51 grams of triethanolamine (0.33 mole) in 277 grams of 50—50 water isopropanol mixture were substituted for the original quantities. The properties of the product had no detectable differences from the product of Example VIII with respect to anti-microbial activity, hair-care, and water treatment properties.

EXAMPLE XII

The process described in Example IX was repeated except that 139 grams of 1,3-bis-dimethylamino-2-propanol (0.95 mole) and 7.6 grams of triethanolamine, and 275 grams of water were substituted for the original quantities. The properties of the product had not detectable differences from the product of Example VIII with respect to anti-microbial activity, hair-care, and water treatment.

EXAMPLE XIII

Polymeric quaternary ammonium products were prepared in about 50% solids solution by using the process described in Example IX, with quantities of reactants indicated by the table below:

|     | BIS-AMINE | MONO-AMINE | 1,3-DICHLORO-2-PROPANOL | SOLVENT |
| --- | --- | --- | --- | --- |
| (a) | 1,3-bis-(octyl methylamino)-2-propanol 56 grams (0.18 mole) | Triethanol-amine 3 gm (0.02 mole) | 25.8 grams (0.2 mole) | 85 grams (50–50)$H_2O$/isopropanol |
| (b) | 1,3-bis-(N-morpholino)-2-propanol 37 grams (0.14 moles) | Triethanol-amine 9 gm (0.06 mole) | 25.8 grams (0.2 mole) | 72 grams (50–50)$H_2O$/isopropanol |
| (c) | 1,3-bis-(Dimethylamino)-2-propanol 23.5 grams (0.16 moles) | Octyl Dimethyl-amine 6 gm (0.04 mole) | 25.8 grams (0.2 mole) | 55 grams of water |
| (d) | 1,3-bis-(diethylamino)-2-propanol 24.5 grams (0.12 moles) | Triethanol-amine 12 gm (0.08 mole) | 25.8 grams (0.2 mole) | 62 grams of water |
| (e) | 1,3-bis-(dimethylamino)-2-propanol 265 grams (0.18 moles) | N-methyl morpholine 2 gm (0.02 mole) | 25.8 grams (0.2 mole) | 55 grams of water |
| (f) | 1,3-bis-(dimethylamino)-2-propanol 26.5 grams (0.18 moles) | N-methyl piperidine 2 gm (0.02 mole) | 25.8 grams (0.2 mole) | 55 grams (50–50)$H_2O$/isopropanol |
| (g) | 1,3-bis-(dimethylamino)-2-propanol 24.0 grams (0.167 moles) | Trimethylamine 2 gm (0.033 mole) | 25.8 grams (0.2 mole) | 52 grams of water |
| (h) | 1,3-bis-(dimethylamino)-2-propanol 26.5 grams (0.18 mole) | Triethanol amine 3 gm (0.02 mole) | 25.8 grams (0.2 mole) | 56 grams of water |

The following table lists the products which were prepared, and the example numbers which disclose their preparation.

(1) $R^I$ equals $R^{II}$ equals $-CH_3$; $R^{III}$ equals $R^{IV}$ equals $R^V$ equals $-CH_3$ — Examples III, IV, XIII g (2) $R^I$ equals $R^{II}$ equals $-CH_3$; $R^{III}$ equals $R^{IV}$ equals $R^V$ equals $-CH_2CH_2OH$ — Examples IX, X XI, XIII h (3) $R^I$ equals $R^{II}$ equals $-CH_3$; $NR^{III}R^{IV}R^V$ equals 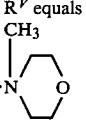 — Examples VI, XIII e Example VII (4) 

| | Example VIII |
|---|---|
| (5) $R^I R^{II} N$ equals 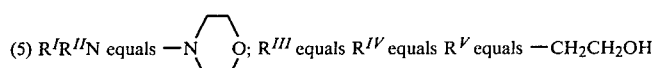; $R^{III}$ equals $R^{IV}$ equals $R^V$ equals $-CH_2CH_2OH$ | |
| (6) $R^I$ equals $-CH_3$, $R^{II}$ equals $-C_8H_{17}$; $R^{III}$ equals $R^{IV}$ equals $R^V$ equals $-CH_2CH_2OH$ | Example XIII a |
| (7) $R^I$ equals $R^{II}$ equals $-CH_3$; $R^{III}$ equals $R^{IV}$ equals $-CH_3$; $R^V$ equals $-C_8H_{17}$ | Example XIII c |
| (8) $R^I$ equals $R^{II}$ equals $-C_2H_5$; $R^{III}$ equals $R^{IV}$ equals $R^V$ equals $-CH_2CH_2OH$ | Example XIII d |
| | Example XIII f |
| (9) $R^I$ equals $R^{II}$ equals $-CH_3$; $NR^{III}R^{IV}R^V$ equals 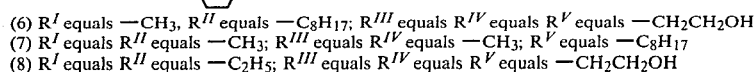 | |

The invention claimed is:

1. A polymeric product having the formula:

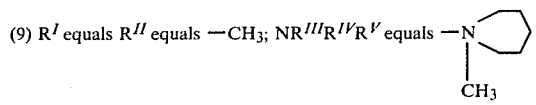

in which $R^I$ and $R^{II}$ are (I) the same or different monovalent, branched or unbranched, alkyl groups of from 1 to 18 carbon atoms, optionally substituted by from 1 to 2 hydroxyl groups; or (II) form a 5, 6 or 7 membered monoheterocyclic ring when taken together with N, or (III) form the N-morpholino group when taken together with N and an oxygen atom; wherein $R^{III}$, $R^{IV}$ and $R^V$ are (I) the same or different, branched or unbranched, alkyl groups of from 1 to 18 carbon atoms optionally substituted by 1 or 2 hydroxyl groups or (II) $R^{III}$ is a branched or unbranched alkyl group of from 1 to 18 carbon atoms optionally substituted by 1 or 2 hydroxyl groups, and $R^{IV}$ and $R^V$ form a 5, 6 or 7 membered monoheterocyclic ring when taken together with N; or (III) $R^{III}$ is a branched or unbranched alkyl group of from 1 to 18 carbon atoms optionally substituted by 1 or 2 hydroxyl groups and $R^{IV}$ and $R^V$ form the N-morpholino group when taken together with N and an oxygen atom; wherein X is a halogen of atomic weight above 30; and wherein n is an integer of from 2 to 20.

2. The product of claim 1 in which $R^I = R^{II} = -CH_3$.

3. The product of claim 1 in which $R^I = R^{II} = -C_2H_5$.

4. The product of claim 1 in which $R^I = -CH_3$ and $R^{II} = -C_8H_{17}$.

5. The product of claim 1 in which

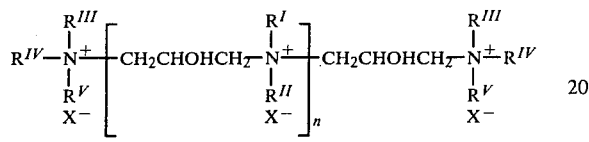

6. The product of claim 2 in which $R^{III} = R^{IV} = R^V = -CH_3$.

7. The product of claim 2 in which $R^{III} = R^{IV} = R^V = -CH_2CH_2OH$.

8. The product of claim 2 in which

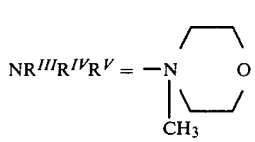

9. The product of claim 2 in which

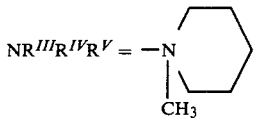

10. The product of claim 3 in which $R^{III} = R^{IV} = R^V = -CH_2CH_2OH$.

11. The product of claim 4 in which $R^{III} = R^{IV} = R^V = -CH_2CH_2OH$.

12. The product of claim 5 in which $R^{III} = R^{IV} = R^V = -CH_3$.

13. The product of claim 5 in which $R^{III} = R^{IV} = R^V = -CH_2CH_2OH$.

14. The product of claim 2 in which $R^{III} = R^{IV} = -CH_3$, and $R^V = -C_8H_{17}$.

15. A method of inhibiting microorganisms which comprises applying the product of claim 1 in a carrier to said microorganisms in an amount sufficient to inhibit their growth.

16. A method of inhibiting microorganisms which comprises applying the product of claim 2 in a carrier to said microorganisms in an amount sufficient to inhibit their growth.

17. A method of inhibiting microorganisms which comprises applying the product of claim 3 in a carrier to said microorganisms in an amount sufficient to inhibit their growth.

18. A method of inhibiting microorganisms which comprises applying the product of claim 4 in a carrier to said microorganisms in an amount sufficient to inhibit their growth.

19. A method of inhibiting microorganisms which comprises applying the product of claim 5 in a carrier to said microorganisms in an amount sufficient to inhibit their growth.

20. A method of inhibiting microogranisms which comprises applying the product of claim 6 in a carrier to said microorganisms in an amount sufficient to inhibit their growth.

21. A method of inhibiting microorganisms which comprises applying the product of claim 7 in a carrier to said microorganisms in an amount sufficient to inhibit their growth.

22. A method of inhibiting microorganisms which comprises applying the product of claim 8 in a carrier to said microorganisms in an amount sufficient to inhibit their growth.

23. A method of inhibiting microorganisms which comprises applying the product of claim 9 in a carrier to said microorganisms in an amount sufficient to inhibit their growth.

24. A method of inhibiting microorganisms which comprises applying the product of claim 10 in a carrier to said microorganisms in an 25. A method of inhibiting microorganisms which comprises applying the product of claim 11 in a carrier to said microorganisms in an amount sufficient to inhibit their growth.

26. A method of inhibiting microorganisms which comprises applying the product of claim 12 in a carrier to said microorganisms in an amount sufficient to inhibit their growth.

27. A method of inhibiting microorganisms which comprises applying the product of claim 13 in a carrier to said microorganisms in an amount sufficient to inhibit their growth.

28. A method of inhibiting microorganisms which comprises applying the product of claim 14 in a carrier to said microorganisms in an amount sufficient to inhibit their growth.

29. A method of conditioning hair which comprises applying a conditioningly effective amount of the product of claim 1 in a carrier to the hair.

30. A method of conditioning hair which comprises applying a conditioningly effective amount of the product of claim 2 in a carrier to the hair.

31. A method of conditioning hair which comprises applying a conditioningly effective amount of the product of claim 3 in a carrier to the hair.

32. A method of conditioning hair which comprises applying a conditioningly effective amount of the product of claim 4 in a carrier to the hair.

33. A method of conditioning hair which comprises applying a conditioningly effective amount of the product of claim 5 in a carrier to the hair.

34. A method of conditioning hair which comprises applying a conditioningly effective amount of the product of claim 6 in a carrier to the hair.

35. A method of conditioning hair which comprises applying a conditioningly effective amount of the product of claim 7 in a carrier to the hair.

36. A method of conditioning hair which comprises applying a conditioningly effective amount of the product of claim 8 in a carrier to the hair.

37. A method of conditioning hair which comprises applying a conditioningly effective amount of the product of claim 9 in a carrier to the hair.

38. A method of conditioning hair which comprises applying a conditioningly effective amount of the product of claim 10 in a carrier to the hair.

39. A method of conditioning hair which comprises applying a conditioningly effective amount of the product of claim 11 in a carrier to the hair.

40. A method of conditioning hair which comprises applying a conditioningly effective amount of the product of claim 12 in a carrier to the hair.

41. A method of conditioning hair which comprises applying a conditioningly effective amount of the product of claim 13 in a carrier to the hair.

42. A method of conditioning hair which comprises applying a conditioningly effective amount of the product of claim 14 in a carrier to the hair.

43. A method of treating water to cause flocculation which comprises applying to an aqueous system an amount of the product of claim 1 sufficient to effect flocculation of suspended materials in the aqueous system.

44. A method of treating water to cause flocculation which comprises applying to an aqueous system an amount of the product of claim 2 sufficient to effect flocculation of suspended materials in the aqueous system.

45. A method of treating water to cause flocculation which comprises applying to an aqueous system an amount of the product of claim 3 sufficient to effect flocculation of suspended materials in the aqueous system.

46. A method of treating water to cause flocculation which comprises applying to an aqueous system an amount of the product of claim 4 sufficient to effect flocculation of suspended materials in the aqueous system.

47. A method of treating water to cause flocculation which comprises applying to an aqueous system an amount of the product of claim 5 sufficient to effect flocculation of suspended materials in the aqueous system.

48. A method of treating water to cause flocculation which comprises applying to an aqueous system an amount of the product of claim 6 sufficient to effect flocculation of suspended materials in the aqueous system.

49. A method of treating water to cause flocculation which comprises applying to an aqueous system an amount of the product of claim 7 sufficient to effect flocculation of suspended materials in the aqueous system.

50. A method of treating water to cause flocculation which comprises applying to an aqueous system an amount of the product of claim 8 sufficient to effect flocculation of suspended materials in the aqueous system.

51. A method of treating water to cause flocculation which comprises applying to an aqueous system an amount of the product of claim 9 sufficient to effect flocculation of suspended materials in the aqueous system.

52. A method of treating water to cause flocculation which comprises applying to an aqueous system an amount of the product of claim 10 sufficient to effect flocculation of suspended materials in the aqueous system.

53. A method of treating water to cause flocculation which comprises applying to an aqueous system an amount of the product of claim 11 sufficient to effect flocculation of suspended materials in the aqueous system.

54. A method of treating water to cause flocculation which comprises applying to an aqueous system an amount of the product of claim 12 sufficient to effect flocculation of suspended materials in the aqueous system.

55. A method of treating water to cause flocculation which comprises applying to an aqueous system an amount of the product of claim 13 sufficient to effect flocculation of suspended materials in the aqueous system.

56. A method of treating water to cause flocculation which comprises applying to an aqueous system an amount of the product of claim 14 sufficient to effect flocculation of suspended materials in the aqueous system.

* * * * *

UNITED STATES PATENT OFFICE
CERTIFICATE OF CORRECTION

Patent No. 4,325,940          Dated April 20, 1982

Inventor(s) Green et al

It is certified that error appears in the above-identified patent and that said Letters Patent are hereby corrected as shown below:

The formula in claim 7 should read:

$$R^{III} = R^{IV} = R^V = -CH_2CH_2OH$$

Signed and Sealed this

Third Day of August 1982

[SEAL]

Attest:

GERALD J. MOSSINGHOFF

Attesting Officer    Commissioner of Patents and Trademarks